(12) United States Patent
Koers

(10) Patent No.: US 10,981,112 B2
(45) Date of Patent: Apr. 20, 2021

(54) FILTER MATERIAL, DEVICE AND METHOD FOR PURIFYING GASES AND LIQUIDS

(71) Applicant: Bonno Koers, Doesburg (NL)

(72) Inventor: Bonno Koers, Doesburg (NL)

( * ) Notice: Subject to any disclaimer, the term of this patent is extended or adjusted under 35 U.S.C. 154(b) by 112 days.

(21) Appl. No.: 15/498,279

(22) Filed: Apr. 26, 2017

(65) Prior Publication Data

US 2018/0311614 A1 Nov. 1, 2018

(51) Int. Cl.
| | |
|---|---|
| *B01D 53/85* | (2006.01) |
| *C02F 3/04* | (2006.01) |
| *B01D 46/52* | (2006.01) |
| *C02F 3/10* | (2006.01) |
| *C12N 11/08* | (2020.01) |
| *C02F 101/32* | (2006.01) |
| *C02F 3/06* | (2006.01) |
| *C02F 3/34* | (2006.01) |
| *C02F 101/10* | (2006.01) |

(52) U.S. Cl.
CPC ............ *B01D 53/85* (2013.01); *B01D 46/521* (2013.01); *C02F 3/04* (2013.01); *C02F 3/101* (2013.01); *C02F 3/103* (2013.01); *C12N 11/08* (2013.01); *B01D 2257/304* (2013.01); *B01D 2257/308* (2013.01); *B01D 2257/708* (2013.01); *B01D 2258/05* (2013.01); *B01D 2258/06* (2013.01); *C02F 3/06* (2013.01); *C02F 3/345* (2013.01); *C02F 2101/101* (2013.01); *C02F 2101/322* (2013.01)

(58) Field of Classification Search
CPC ........ B01D 53/78; B01D 53/85; C12M 25/18; C02F 3/101
See application file for complete search history.

(56) References Cited

U.S. PATENT DOCUMENTS

| | | | | |
|---|---|---|---|---|
| 3,347,381 | A * | 10/1967 | Minch | C02F 3/101 |
| | | | | 210/150 |
| 5,348,654 | A * | 9/1994 | Fischer | C02F 3/043 |
| | | | | 210/151 |
| 5,714,379 | A | 2/1998 | Phipps, Jr. | 435/266 |
| 6,194,198 | B1 | 2/2001 | Koers | 435/266 |
| 6,283,309 | B1 | 9/2001 | Koers | 210/488 |
| 6,696,284 | B2 * | 2/2004 | Haridas | B01D 53/84 |
| | | | | 435/266 |
| 2005/0250201 | A1 | 11/2005 | Daly | 435/299.1 |

(Continued)

FOREIGN PATENT DOCUMENTS

| | | | | |
|---|---|---|---|---|
| EP | 0190801 | | 8/1986 | ............ C12M 1/00 |
| EP | 1157732 | | 11/2001 | ............ B01D 53/85 |
| FR | 2051381 | | 4/1971 | ............ C02F 3/10 |

(Continued)

OTHER PUBLICATIONS

European Search Report issued in application No. 18169174.2, dated Sep. 3, 2018 (6 pgs).

*Primary Examiner* — William H. Beisner
(74) *Attorney, Agent, or Firm* — Hayes Soloway P.C.

(57) ABSTRACT

The present disclosure relates to a filter material which can be used in reducing the content of contaminants in a raw gas or liquid and a device which comprises the filter material. The disclosure also relates to a method for reducing the content of contaminants in a raw gas or liquid which applies the filter material and/or device.

22 Claims, 2 Drawing Sheets

(56) References Cited

U.S. PATENT DOCUMENTS

2006/0042209 A1     3/2006    Dallas et al. .................... 55/524
2010/0089818 A1     4/2010    Koers ........................... 210/488

FOREIGN PATENT DOCUMENTS

| | | | |
|---|---|---|---|
| GB | 1281874 | 7/1972 | ............... C02C 1/04 |
| GB | 2162833 | 2/1986 | ............... C02F 3/10 |
| NL | 1007019 | 3/1999 | ............ B01D 53/85 |
| WO | WO-9318800 A1 * | 9/1993 | ............... A61L 9/16 |
| WO | WO2006009427 | 1/2006 | ............ B01D 46/24 |
| WO | WO2013093155 | 6/2013 | ............ B01D 53/84 |
| WO | WO2016204616 | 12/2016 | ............ B01D 53/52 |

* cited by examiner

FILTER MATERIAL, DEVICE AND METHOD FOR PURIFYING GASES AND LIQUIDS

The present invention relates to a filter material which can be used in reducing the content of contaminants in a raw gas or liquid and a device which comprises said filter material. The invention also relates to a method for reducing the content of contaminants in a raw gas or liquid which applies said filter material and/or device.

INTRODUCTION

This invention relates to a filter material, device and method for treatment of gas or liquid mixtures and in particular for removing contaminants from a gas or liquid which contains contaminants.

The invention is applicable to waste water or air or gas produced from any industrial process. Gas and liquid media produced and used in industry may contain contaminants. Examples of such gas or liquid media include waste water, flare gas and biogas. For instance, biogas is a gas mixture that can be produced by anaerobic digestion with anaerobic bacteria, which break down the organic carbon in the raw materials to a biogas which is mainly comprised of methane ($CH_4$) but which contains contaminants such as carbon dioxide ($CO_2$) nitrogen ($N_2$) and hydrogen sulphide ($H_2S$). $H_2S$ is very harmful to the environment and human health.

There is a continuous need in industry for improved methods and devices which remove contaminants from gas or liquid mixtures.

For this purpose it is common in industry to apply micro-organisms that are capable of remove contaminants. The micro-organisms are adhered in biofilms onto filter materials. The contaminated gas of liquid stream can be passed through or along these filter materials, so that the micro-organisms can exert their purifying action. After passing the filter this will result in a liquid or gaseous stream with reduced concentrations of contaminants.

In a device as described in EP 0 190 801 A1, as a filter material a polyurethane foam mat is employed, wherein one side is flat and its other side is provided with cone like projecting portions. The mat has good adhesive properties for micro-organisms. A number of such mats are placed on top of each other so that a plane surface of one mat contacts a surface with projecting portions of the mat lying on it. Due to this, a certain free space remains between successive mats. Although a purifying result may be achieved, there is a difficulty that the medium flowing through and along the mats experiences a considerable flow resistance. Moreover there is a considerable risk of clogging, which further increases the flow resistance, which in its turn leads to inefficient purification.

U.S. Pat. No. 6,283,309 of the present inventor discloses a filter material being a mat having large open pores and being made of foamed plastic material; said mat being intended for absorbing micro-organisms; said mat of foamed plastic material having a flat surface on both sides; said mat being rolled-up with a supporting element made of at least partly-undulated, mutually connected, resilient threads, in such a way that a certain distance between parts of the mat radially following one another remains free by the presence of the supporting element. Although a good purifying result is obtained with these mats, there is still room for improvement with respect to reducing flow resistance, clogging and enhancing purification efficiency.

Using a rolled up foamed plastic material in a biological filter is also described in GB 1 281 874 (A). There, strips of material are wound in such a way, that successive windings are spaced apart across some distance. To that end, the strip is heated during rolling it up, so that a more or less stiff unity is achieved. The filter can only be used with relatively small dimensions of the strip. Moreover, the material only has a limited surface per unit of volume so that the purification efficiency will be far from optimal.

A further rolled-up strip is known from FR 2 051 381 (A), wherein a foil of plastic and an undulated foil are rolled-up together, so that continuous channels are achieved. The inventor has found that rolls with this configuration also have disadvantages. In particular, it appears that the channels of consecutive layers of a roll slide into each other because pressures may cause the contact surfaces between the flat foil and the undulated foil to slide sidewards. It also appears that during rolling and packing the rolled up strip channels collapse. This will lead to unfavorable dimensions of the channels resulting in an increase of flow resistance and clogging, which in its turn further increases the flow resistance. This leads to inefficient purification.

The object of the invention is to remove these difficulties and to provide a filter material which, when used in a method of purifying gases or liquids, leads to reduced flow resistance, reduced clogging and enhanced purification efficiency.

SUMMARY OF THE INVENTION

The aim of the invention has been achieved by the provision of a filter material which has a first sheet having a planar surface (i.e. sheet without undulations) and a second sheet having an surface of undulations (i.e. a sheet with undulations), wherein said second sheet is fixedly attached to the first sheet at the contact surface between the first sheet and each undulation of the second sheet, so that continuous channels of fixed dimensions are formed between the first and second sheet.

Therefore, in a first aspect the invention relates to a filter material, comprising a first sheet of a plastic which is suitable for attachment of micro-organisms thereto, which has a planar surface; and a second sheet of a plastic which is suitable for attachment of micro-organisms thereto, which has a surface of undulations arranged in a parallel fashion with respect to each other wherein said second sheet extends over the surface of the first sheet, wherein said second sheet is fixedly attached to the first sheet at the contact surface between the first sheet and each undulation of the second sheet, so that continuous channels are formed between the first and second sheet.

In a second aspect the invention relates to a device for purifying a gas or a liquid medium, comprising a chamber; an inlet for passing the medium into the chamber; an outlet for passing the medium out of the chamber; and at least one cylinder of rolled-up filter material according to the first aspect of the invention positioned in said chamber.

In a third aspect the invention relates to a method for reducing the content of a contaminant in a gas or liquid medium, comprising the steps of applying a biomass in the form of a graft in the channels of filter material according to the first aspect of the invention to obtain channels covered with a biofilm of microorganisms capable of degrading said contaminant; and passing a gas or liquid medium stream containing said contaminant through the biofilm covered channels such that a product stream comprising lower content of said contaminant compared to the medium stream is obtained after passage through said channels.

SHORT DESCRIPTION OF THE FIGURES

FIGS. 1A and B show a cross-sectional view of two embodiments of the filter material in accordance with the invention.

DETAILED DESCRIPTION

Figure 1A:
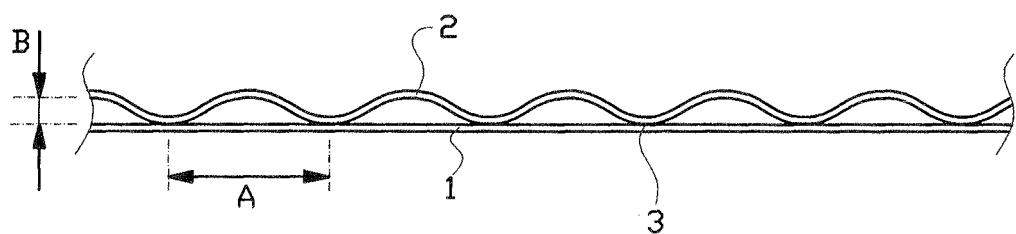

In accordance with the invention a filter material is provided which has a first sheet having a planar surface and a second sheet having a surface of undulations. The second sheet is fixedly attached to the first sheet at the contact surface between the first sheet and each undulation of the second sheet, so that a mat is formed with continuous channels between the first and second sheet. This mat can be rolled up to form a cylinder.

Because the undulated second sheet is fixedly attached to the first sheet which does not have undulations (flat sheet) at the contact surface between the first flat sheet and each undulation of the undulated sheet, the contact surfaces between the flat sheet and the undulated sheet cannot slide sidewards. This way the channels of consecutive sheets of a rolled up mat cannot slide into each other. The inventor has found that this has the effect that during rolling and packing of the material the channels remain their shape and dimensions, without losing flexibility so that the filter mat can easily be rolled into a cylinder. Because of this predetermined dimensions of the channels designed for optimal flow and purification are maintained at all times. This leads to increased contact surface area, lower exchange times of the raw medium with the micro-organisms and increased purification/polishing capacity.

When material accumulates in a filter, this will lead to a loss of pressure, i.e. a pressure drop. The pressure drop increases when a filter clogs. A high pressure drop indicates therefore low efficiency of a filter. The inventor has surprisingly observed that with the filter material of the invention, it is possible to maintain a steady low pressure drop over the material for a prolonged period of times.

Further, because channels remain their shape and dimensions at all times, the surface per unit volume of filter material becomes more controllable.

Because optimal flow can be maintained for a longer time, the requirement of washing the filter material is reduced to a minimum. This prevents downtime of the purification system. As a result costs for maintenance are significantly reduced. As an additional effect the filter material of the invention also has a longer lifetime compared to other materials.

The filter material has also increased strength compared to materials of similar construction wherein the flat and undulated sheets are not fixedly attached at the contact surfaces between the flat sheet and the undulated sheet. This makes the filter material of the invention easy to handle. Because the shape and dimensions of the channels are fixed at all time rolling and packing also does not require particular precautions to ensure acceptable channel dimensions.

The filter material of the invention is produced in the form of a mat. The sheets have flexibility properties which enable the mat of filter material to be rolled to form a cylinder of filter material. In order to achieve this, the plastic of said filter material should be made of a suitable plastic which also allows adherence of micro-organisms. A preferred suitable plastic comprises polyethylene or polypropylene or a combination thereof. Micro-organisms adhere well to these materials and these plastics provide sufficient strength and flexibility, so that relatively thin sheets of material can be used, so that a higher surface per unit of volume can be used to be covered with micro-organisms.

In the filter material the second sheet is preferably fixedly attached to the first sheet at the contact surface between the first and second sheet by means of a weld, because this gives a strong and fixed connection between the plastic sheets. The weld may suitably be realized by melting. It is preferred that the weld extends over the full length of the contact surfaces, because this gives optimal strength to the connection between the two sheets.

In order to provide optimal surface per unit of volume of filter material the undulations of the second sheet of the material preferably have a zigzag or V shape or sinusoidal configuration.

For the same reason it is preferred that a mat of filter material in accordance with the invention does not comprise further sheets. In other words, it is preferred that a mat of filter material consists of said first sheet and said second sheet.

When in use, the filter material of the invention is preferably in the form of a cylinder with open pores that are formed by the continuous channels between the two sheets that extend along the longitudinal axis of said cylinder. This is achieved by rolling up a mat of the filter material of the invention.

The continuous channels may extend along the longitudinal axis of said cylinder in a helical way, but it is preferred that the continuous channels extend parallel to the longitudinal axis of the cylinder, because this provides optimal strength to the cylinder. In fact, when cylinders with channels extending parallel to the longitudinal axis of the cylinder are used in a purification device, a person may be able to stand on a vertically mounted cylinder, for instance in case of maintenance of said device, without running a risk that the cylinder collapses.

The filter material of the invention is in particular suitable for reducing the content of contaminants in a raw gas or liquid medium. Therefore, when in use it is preferred that in the filter material of the invention the channels are covered with a biofilm of contaminant degrading microorganisms.

Because the filter material of the invention is less prone to clogging and shows a steady very low pressure drop over prolonged time periods compared to prior art filter materials as discussed above, the filter material of the invention can be used in combination with growing biomass. In particular when a medium contains volatile organic compounds (VOCs) the biomass on the filter material grows fast. In prior art systems this would inevitably lead to fast clogging of the filter material in due course, necessitating the need for washing and/or replacement of the filter material. Because of the stable pressure drop due to the filter material of the invention, removal of VOCs can be performed efficiently and the requirement for washing and/or replacement of filter material will be reduced to a minimum. The filter material of the invention is therefore very suitable for reducing the content of VOCs. Such VOCs include aromatic compounds such as benzene, toluene and xylenes. When in use for this purpose the filter material of the invention the channels will be covered with a biofilm of VOC degrading microorganisms. Such microorganisms include for instance bacteria from the *Pseudomonas* genus.

The filter material of the invention is also suitable for reducing the content of sulphuric compounds, such as $H_2S$ or $CS_2$, in a raw gas or liquid medium. Therefore, when in use for this purpose the filter material of the invention channels will be covered with a biofilm of sulphuric compound (such as $H_2S$ and/or $CS_2$) degrading microorganisms. Such bacteria or mixtures of bacteria are known in the art for purposes of removing sulphuric compounds from gases, liquids or fluids, and may for example include bacteria belonging to the *Thiobacillus* genus.

The filter material is suitable for purifying a gas or a liquid medium in a method for reducing the content of contaminants in a raw gas or liquid medium. In this respect, the invention also provides for a method comprising the steps of applying a biomass in the form of a graft in the channels of the filter material in accordance with the invention to obtain channels covered with a biofilm of contaminant degrading microorganisms; and passing a raw gas or liquid medium stream containing contaminants through the biofilm covered channels such that a product stream comprising lower contaminants content compared to the raw medium stream is obtained after passage through said channels. Regarding the present invention the contaminant may suitably be selected from the group consisting of sulphuric compounds, such as $H_2S$ and/or $CS_2$ and volatile organic compounds.

As mentioned above the micro-organisms may include anaerobic and aerobic micro-organisms or a mixture thereof. To optimize the microbial action it is preferred that the method further comprises regulation of the level of oxygen in the stream passing through the filter. This way the conditions under which the micro-organisms optimally perform their contaminant removing activity can be regulated.

Although in principle the method of the invention does not require washing of the filter material, as a matter of precaution to ensure optimal performance stability, the filter material may be washed after a certain period of operation. For this purpose, a washing solution is passed through the channels of the filter material. It is preferred that the washing solution is not based on a soap because that would wash too much of the biomass away. Instead, the inventor has surprisingly found that when a washing step is performed with an alkaline solution, biomass is washed away to acceptable levels and that the system is operable at full efficiency again within 3 days. The method of the invention therefore may further comprise a periodical washing step of passing a washing solution through the biofilm covered channels of the filter material, wherein said washing solution is an alkaline solution.

The method of the invention and the filter material of the invention are preferably applied in the device of the invention. This device comprises a chamber; an inlet for passing the medium into the chamber; an outlet for passing the medium out of the chamber; and at least one cylinder of rolled-up filter material in accordance with the invention positioned in said chamber. This cylinder is fittingly placed in said chamber, optionally by means of a container construction, such as a pipe. In this case the cylinder is fittingly positioned in a pipe, which pipe is positioned in said chamber.

A device in accordance with the invention can be used for purifying air containing contaminants. In this case water will be sprayed onto the cylindrical mat from above, so that the water consumption is reduced to a minimum. There, the air will be led through the chamber from the bottom to the top. In the device means for keeping or bringing the pH-value of the recirculated water at the desired value can be present. It is also possible to add nutrients to the water for an optimum biological purification of the air flowing through the device.

The device can also be provided with measuring equipment for the temperature, the salinity and the pressure drop. By this, the conditions of the surroundings for the micro-organisms can be monitored.

The device can also be used for purifying water. The water can flow through the device from the top to the bottom and air can be brought into the lower part of the chamber so that it will flow through the water to be purified from the bottom to the top.

Washing can be done inside the device of the invention, without the need to remove the filter material. For this purpose it is preferred that air is bypassed over the device, while a washing solution is passed through the channels of the filter material. To enable washing steps without the necessity to remove filter rolls the device may be provided with an air bypass line configured between the air inlet and the air outlet of the device.

The device preferably comprises multiple cylinders of filter material in accordance with the invention. This makes maintenance easy and allows for regulation of purification steps by varying the pore size between different cylinders. In general when multiple cylinders are used it is preferred that the first cylinder through which the raw medium stream (gas or liquid) is intended to pass has rather large pores. This way there is more space for biomass to accumulate without having detrimental effects on the flow. A major portion of the contaminants can be removed in this cylinder. After removal of the major portion of contaminants, the medium stream is passed to a next cylinder wherein the medium stream is polished, i.e. where residual contaminants are removed. Removal of low concentrations of residual contaminants requires more contact with the contaminant degrading microorganisms. Therefore, the next cylinder through which the raw medium stream is intended to pass, i.e. the cylinder downstream of the first cylinder, preferably has smaller pores, making it in particular suitable for a polishing step that allows removal of residual contaminants after the previous purification stage(s). In a device with multiple cylinders it is therefore preferred that a cylinder positioned downstream of another of said cylinders has pores that have a smaller cross-section in the circumferential plane of the cylinders than the pores of the adjacent cylinder positioned upstream of it.

The invention will now be further explained by way of the drawings. The drawings are meant to illustrate the principle of the invention and should not be interpreted as limiting the scope of the claims.

Figure 1B:
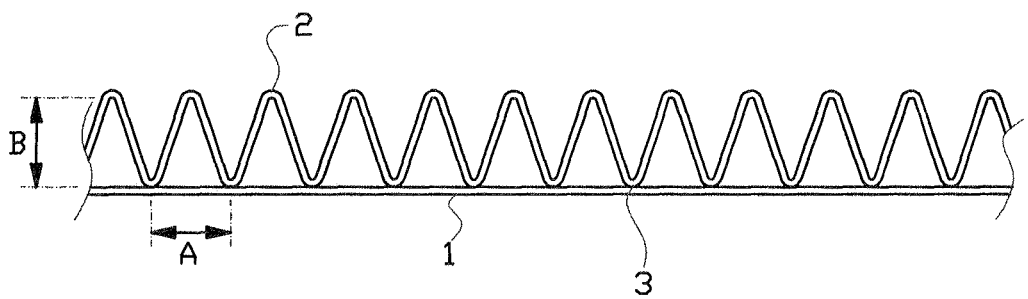

FIGS. 1A and B show two embodiments of the filter material of the invention. The filter material is produced as a mat. The mat of filter material has a first sheet 1 with a planar surface of a plastic which is suitable for attachment of micro-organisms thereto and a second sheet 2 which has a surface of undulations arranged in a parallel fashion with respect to each other. Also the second sheet 2 is made of a plastic which is suitable for attachment of micro-organisms thereto. Without limitation, such plastics may comprise or consist of polyethylene, polypropylene or mixtures thereof. The undulations may have a sinusoidal shape as shown in FIG. 1A or a zigzag or V shape as shown in FIG. 1B. The undulated second sheet 2 extends over the surface of the first sheet 1 and is fixedly attached, for instance by means of a weld over the full length of the contact surface 3, to the first sheet 1 at the contact surface 3 between the first sheet and each undulation of the second sheet 2, so that continuous channels are formed between the first and second sheet (1, 2). Suitable pore dimensions may range from 0.75 to 3 cm in direction A and from 0.5 to 2 cm in direction B. A suitable thickness of the sheets may be between 0.5 and 2.5 mm, preferably approximately 1 mm.

Figure 2A:
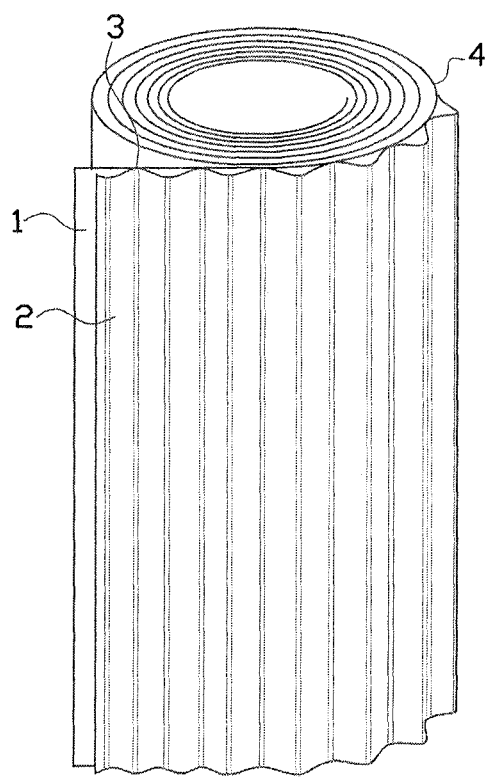
FIG. 2A shows a simplified representation of an embodiment of rolled-up filter material in accordance with the invention.
Figure 2B:
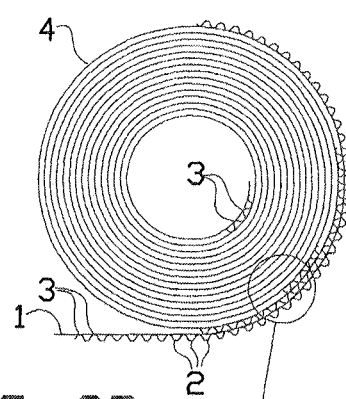
FIG. 2B shows a top view of this rolled up material and FIG. 2C shows an enlarged part of the top view of FIG. 2B.
Figure 2C:
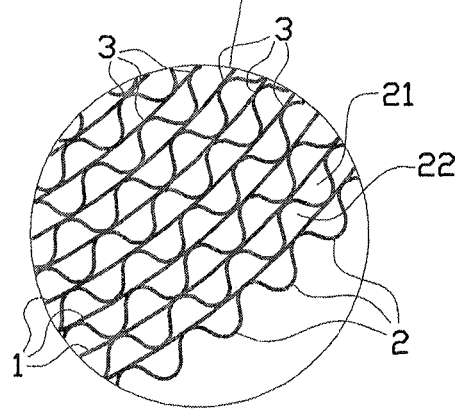

As shown in FIG. 2A-C, the mat of filter material may be rolled for use to form a cylinder 4 with open pores formed by the continuous channels that extend along the longitudinal axis of said cylinder. From top view as shown in FIGS. 2B and 2C it can be seen that in the cylinder of FIG. 2A open pores (21, 22) are formed by the continuous channels that extend along the longitudinal axis of said cylinder. Because the undulated second sheet 2 is attached at the contact surface 3 between the first flat sheet 1 and each undulation of the undulated sheet 2, sliding of the contact surfaces 3 between the flat sheet 1 and the undulated sheet 2 is prevented so that the channels of consecutive sheets of a roll cannot slide into each other. Because of this predetermined dimensions of the channels designed for optimal flow and purification are maintained at all times, leading to increased surface area, lower exchange times of raw medium with micro-organisms adhered to the surface of the channels, and increase of purification/polishing capacity.

Figure 3:
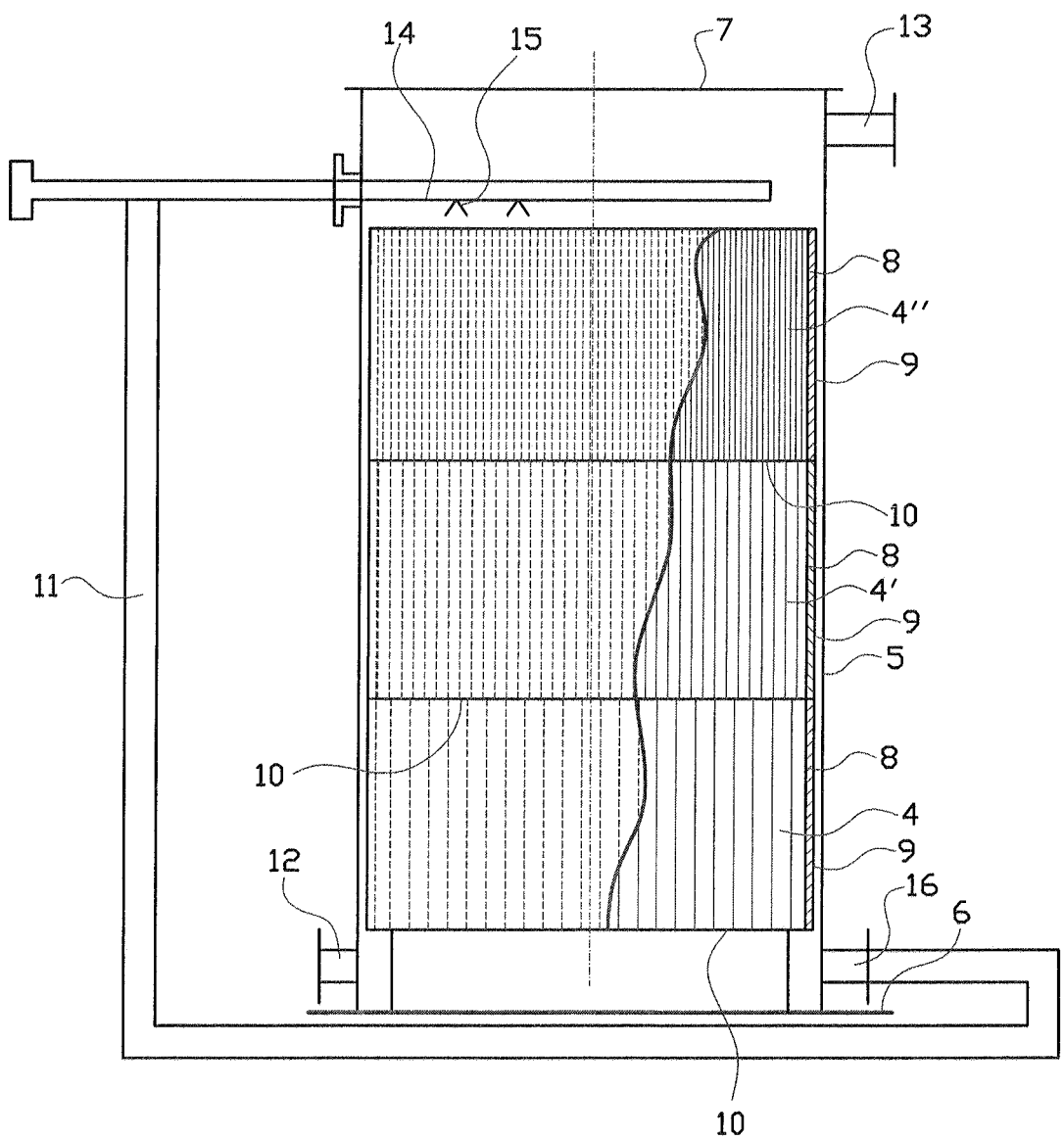
FIG. 3 shows a simplified representation of an embodiment of the device in accordance with the invention.

In order to be used in purifying raw gas or liquid mixtures cylinders 4, 4', 4" of rolled up filter mats can be mounted into a purification device. An example of such a device adapted for purifying contaminated air is shown in FIG. 3. The device illustrated in FIG. 3 comprises a cylindrical chamber 5 that can be made of glass-fiber reinforced plastic, for example. This material should preferably be resistive against aggressive acids and biological activity. At its bottom side, the chamber 5 is closed-off by a baseplate 6, and at its top side by a lid 7, which can be pressed against the chamber, e.g. by a number of bolts, for closing it.

Within the chamber 5, there are three filter elements 9, each constituted by a pipe 8 being provided with a framework 10 at its bottom side and accommodating filter material 4, 4, 4". As illustrated in FIG. 2, the filter material 4 is obtained by rolling-up a mat in accordance with the invention.

The rolled-up assemblies 4, 4, 4" of the mat are fittingly mounted in a pipe 8 for constituting a filter element 9.

The lower and upper edge of the stacked pipes 8 of a filter element 9 are designed such that the pipes 8 rest on each other, due to which the wall of the chamber 5 is only loaded to a small degree.

At its bottom side, the chamber 5 is provided with an air intake 12 and at the top side with an air outlet 13 for discharge of purified air.

In general when multiple cylinders are used it is preferred that the first cylinder through which the raw medium stream is intended to pass has rather large pores as explained above. In the depicted embodiment, where raw gas in the form of contaminated air enters the device via intake 12, the lowermost cylinder 4 has the largest pores. The next cylinder through which the raw medium stream is intended to pass, i.e. the cylinder 4' downstream of the first cylinder, may have smaller pores because the amount of large particles will be smaller after passage through. A further downstream cylinder 4" may even have smaller pores.

Above the uppermost cylindrical filter element 9 is a conduit 14 provided with one or more spray nozzles 15 for spraying water on it. At the bottom side of the chamber 5 the water is discharged by means of a conduit 16. The conduit 14 having the spray nozzles 15 can easily be removed when the filter elements 9 are to be replaced.

In case the device shown in FIG. 3 would be used for purifying water, this will be brought onto the uppermost filter element 9 from above. The water will then be distributed across the filter element 9 to flow downwards. Because the water enters from above in the case water would be purified, it is in this case preferred that the cylinder with the largest pores is placed on top, while downstream cylinders would have smaller pore sizes. Referring to FIG. 3 this would mean that cylinders 4, 4' and 4" would be placed in the inverse order in case the device would be configured for purification of raw liquids media such as contaminated water.

The water is discharged from the lower end of the chamber 5. Air can be supplied to the lower end of the chamber 5, in such a way that the air moves upwards through the water. Optional water recirculator 11 may be configured between conduit 16 and conduit 14 for recirculating water from the lower end of the chamber to the spray nozzles.

It will be obvious, that only one single possible embodiment of a device according to the invention has been illustrated in the drawing and that only some possible applications have been described above. Many changes can be made without being beyond the inventive idea as it is defined in the claims.

EXAMPLE

The performance of the filter material of the invention was compared to other filter materials in a system for cleaning biogas.

Prior art filter material A is a cylinder formed of a rolled mat of polyurethane foam with large pores, as described in Dutch patent 1007019.

Filter material B is a cylinder of rolled up plastic (PE/PP) filter material comprising a first sheet of plastic which has a planar surface; and a second sheet of a plastic which has an surface of undulations arranged in a parallel fashion with respect to each other; wherein said second sheet extends over the surface of the first sheet, wherein said second sheet is not fixed to the first sheet at the contact surface between the first sheet and each undulation of the second sheet.

Filter material C is a cylinder of rolled up plastic (PE/PP) filter material according to the invention, which differs from filter material B in that said second sheet is fixedly attached to the first sheet at the contact surface between the first sheet and each undulation of the second sheet. In this embodiment said second sheet is fixedly attached to the first by means of a weld which extends over the full length of said contact surface.

The rolled filter mats were used in devices according to the invention, which in this case were reactors basically as described in FIG. 3.

The filter material was grafted with microorganisms capable of degrading sulphuric components from biogas. The microorganisms were initially supplied with nutrients to start the system. The system was allowed to calibrate until acceptable degrading performance was achieved. At that stage various measurements were taken to determine the performance of the filter materials. The results are shown in table 1 below.

TABLE 1 performance tests of filter materials

|  | Filter material A | Filter material B | Filter material C |
|---|---|---|---|
| Break down capacity (kg sulphur/hour) | 4.8 | 15 | 22 |
| $CS_2$ removal | 65 | 90 | 99.5% |
| $H_2S$ removal | 80 | 99 | 99.95% |
| Pressure drop (pa/month) | 1000 | 50 | 15-18 |

As shown in table 1, it appeared that when filter material A was used pressure drops were measured increasing to 1000 pa in a month time. This led to low cleaning efficiency. In order to be functional the filter material had to be cleaned every month. In the same period use of filter material B lead to an increase of the pressure drop to 50 pa while still increasing in time. In the same period use of filter material C showed the pressure drop increased only to between 15 and 18 pa. In fact, even after approximately 5 months pressure drops were measured for filter material C of only between 30 and 60 pa. This shows that the filter material is less sensible for clogging compared to other filter materials tested and can be used for a very long period without the need to clean the filters. This way the device of the invention can run almost continuously without downtime for cleaning purposes.

As also shown in table 1 the breakdown capacity of sulphuric compound using filter materials A, B and C was compared. It is clear from table 1 that when filter material C was used the best results were obtained. A break down capacity of 22 kg sulphur/hour was obtained with filter C which was a more than 5 fold improvement compared to filter material A and an almost 50% improvement compared to filter material B. Use of filter material C lead to almost 100% removal of $CS_2$ and $H_2S$ from the biogas, which are unprecedented performances in the field of biogas purification. The filter material of the invention therefore shows a significant improvement in purification efficiency.

In summary the filter material of the invention provides per gross volume:
More void volume which allows for optimal contact time of the micro-organisms with the contaminated liquid or gas;
More biological contact surface area which allows for higher breakdown capacity;
Lesser pressure drop;
Higher purification efficiency.

The filter material of the invention also provides a washable filter which allows for higher loadings of organic compounds. The filter can be washed out without replacing or taking out the filter from the device wherein it is mounted, resulting in lesser down time.

The invention claimed is:
1. A device for purifying a gas or a liquid medium, comprising
a chamber;
an inlet for passing the medium into the chamber;
an outlet for passing the medium out of the chamber;
a plurality of cylinders of rolled-up filter material positioned in said chamber;
wherein a cylinder positioned in a downstream direction of another of said cylinders has pores that have a smaller cross-section in a circumferential plane of the cylinders than the pores of an adjacent cylinder positioned in an upstream direction thereof;
and wherein said filter material comprises
a first sheet of a plastic which is suitable for attachment of micro-organisms thereto, which has a planar surface; and
a second sheet of a plastic which is suitable for attachment of micro-organisms thereto, which has a surface of undulations arranged in a parallel fashion with respect to each other;
wherein said second sheet extends over the surface of the first sheet,
wherein said second sheet is fixedly attached to the first sheet at the contact surface between the first sheet and each undulation of the second sheet, so that continuous channels are formed between the first and second sheet; and
wherein said material is rolled-up as a cylinder with open pores that are formed by said continuous channels that extend along a longitudinal axis of said cylinder; and
wherein the channels are covered with a biofilm of contaminant degrading microorganisms.

2. The device according to claim 1, wherein in said filter material, said second sheet is fixedly attached by a weld.

3. The device according to claim 2, wherein in said filter material, the weld extends over a full length of said contact surface.

4. The device according to claim 1, wherein in said filter material, said undulations are in a zigzag or sinusoidal configuration.

5. The device according to claim 1, wherein in said filter material, said continuous channels extend parallel to the longitudinal axis of the cylinder.

6. The device according to claim 1, wherein the plastic of said filter material comprises polyethylene and/or polypropylene.

7. The device according to claim 1, wherein the channels of said filter material are covered with a biofilm of $H_2S$ and/or $CS_2$ degrading microorganisms, or a biofilm of VOC degrading microorganisms.

8. The device of claim 1, wherein the filter material has pore dimensions in the range of 0.75 to 3 cm in a direction (A), by 0.5 to 2 cm in a direction (B).

9. The device of claim 1, wherein the first sheet and the second sheet each have a thickness in the range of 0.5 to 2.5 mm.

10. The device of claim 9, wherein the first sheet and the second sheet each having a thickness of 1 mm.

11. A method for reducing the content of a contaminant in a gas or liquid medium, comprising the steps of:
providing a device comprising:
a chamber,
an inlet for passing the medium into the chamber,
an outlet for passing the medium out of the chamber,
a plurality of cylinders of rolled-up filter material positioned in said chamber,
wherein a cylinder positioned in a downstream direction of another of said cylinders has pores that have a smaller cross-section in a circumferential plane of the cylinders than the pores of an adjacent cylinder positioned in an upstream direction thereof;
and wherein said filter material comprises:
a first sheet of a plastic which is suitable for attachment of micro-organisms thereto, which has a planar surface, and a second sheet of a plastic which is suitable for attachment of micro-organisms thereto, which has a surface of undulations arranged in a parallel fashion with respect to each other, wherein said second sheet extends over the surface of the first sheet, wherein said second sheet is fixedly attached to the first sheet at the contact surface between the first sheet and each undulation of the second sheet, so that continuous channels are formed between the first and second sheet, and wherein said material is rolled-up as a cylinder with open pores that are formed by said continuous channels that extend along a longitudinal axis of said cylinder, and wherein the channels are covered with a biofilm of contaminant degrading microorganisms, applying a biomass in the form of a graft in the channels of filter material in the device to obtain channels covered with a biofilm of microorganisms capable of degrading said contaminant; and passing a gas or liquid medium stream containing said contaminant through the biofilm covered channels such that a product stream comprising lower content of said contaminant compared to the medium stream is obtained after passage through said channels, wherein said medium stream is passed through said plurality of cylinders and wherein a cylinder through which the medium stream passes has pores that have a larger cross-section in the circumferential plane of the cylinder than a next cylinder through which the medium stream is passed.

12. The method according to claim 11, wherein said contaminant is selected from the group consisting of sulphuric compounds and volatile organic compounds.

13. The method according to claim 12, which further comprises regulation of the level of oxygen in the stream.

14. The method according to claim 11, which further comprises regulation of the level of oxygen in the stream.

15. The method according to claim 11, which further comprises a periodical washing step, which comprises passing a washing solution through said biofilm covered channels, wherein said washing solution is an alkaline solution.

16. The method according to claim 11, wherein in said filter material, said second sheet is fixedly attached by a weld.

17. The method according to claim 11, wherein in said filter material, the weld extends over a full length of said contact surface.

18. The method according to claim 11, wherein in said filter material, said undulations are in a zigzag or sinusoidal configuration.

19. The method according to claim 11, wherein in said filter material, said continuous channels extend parallel to the longitudinal axis of the cylinder.

20. The method according to claim 11, wherein the plastic of said filter material comprises polyethylene and/or polypropylene.

21. The method according to claim 11, wherein the microorganisms are $H_2S$ and/or $CS_2$ degrading microorganisms.

22. The method according to claim 11, wherein the microorganisms are VOC degrading microorganisms.

* * * * *